US00PP25319P3

(12) United States Plant Patent

Kardos et al.

(10) Patent No.: US PP25,319 P3

(45) Date of Patent: Mar. 3, 2015

(54) *HYDRANGEA QUERCIFOLIA* PLANT NAMED 'PIIHQ-I'

(50) Latin Name: *Hydrangea quercifolia* Bartr.
Varietal Denomination: PIIHQ-I

(71) Applicants: Joshua H. Kardos, Watkinsville, GA (US); Michael A. Dirr, Bogart, GA (US)

(72) Inventors: Joshua H. Kardos, Watkinsville, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 133 days.

(21) Appl. No.: 13/815,698

(22) Filed: Mar. 14, 2013

(65) Prior Publication Data

US 2014/0283250 P1 Sep. 18, 2014

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para

(74) *Attorney, Agent, or Firm* — Lathrop & Gage LLP

(57) ABSTRACT

A new and distinct cultivar of *Hydrangea quercifolia* plant named 'PIIHQ-I', characterized by its compact, rounded to spreading growth habit; strong stems, even when young, resulting in higher quality finished container plants for the grower; dark green disease resistant foliage; reddish orange to reddish purple fall color; full, white inflorescences that age to light pink and are held upright on the plant.

3 Drawing Sheets

Genus and species of plant claimed: *Hydrangea quercifolia* Bartr.

Variety denomination: 'PIIHQ-I'.

BACKGROUND OF THE INVENTION

The present invention relates to a new and distinct cultivar of *Hydrangea quercifolia,* a member of the Hydrangeaceae family, hereinafter referred to by its cultivar name 'PIIHQ-I'. This cultivar is grown primarily as an ornamental for landscape use. The cultivar originated from an open pollination of an unnamed and unpatented selection of *Hydrangea quercifolia* as part of a breeding program in Watkinsville, Ga. in 2007, and was selected from the progeny by continued evaluation for growth habit, floral and foliage characteristics, and production qualities.

'PIIHQ-I' has been asexually reproduced by softwood cuttings since 2009 in Watkinsville, Ga. The characteristics of the cultivar have been stable and reproduced true to type in successive vegetative generations.

SUMMARY OF THE INVENTION

'PIIHQ-I' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIHQ-I' from all other varieties in commerce known to the inventor. 1) Compact, rounded to spreading growth habit. 2) Strong stems, even when young, resulting in higher quality finished container plants for the grower. 3) Dark green disease resistant foliage. 4) Reddish orange to reddish purple fall color. 5) Full, white inflorescences that age to light pink and are held upright on the plant.

'PIIHQ-I' is distinguished from its female parent by its inflorescence quality, flower color, and its growth habit. 'PIIHQ-I' has full inflorescences (the sepals cover the fertile flowers) that emerge white and eventually age to light pink, and a compact growth habit, whereas its female parent has more open inflorescences (the sepals do not fully cover the fertile flowers) that emerge white and eventually age to brown, and a less compact growth habit.

'PIIHQ-I' can be compared to the cultivar 'Ruby Slippers' (unpatented) but differs in the following characteristics. 'PIIHQ-I' has a compact, but overall larger growth habit than 'Ruby Slippers'. 'PIIHQ-I' has white inflorescences that age to light pink, whereas 'Ruby Slippers' has white inflorescences that age to pink and then deep rose. 'PIIHQ-I' has reddish orange to reddish purple fall color, whereas 'Ruby Slippers' has mahogany-red fall color.

BRIEF DESCRIPTION OF THE DRAWINGS

The accompanying color photographs illustrate the flower and foliage characteristics and the overall appearance of 'PIIHQ-I', showing the colors as true as it is reasonably possible to obtain in color reproductions of this type. Colors in the photographs may differ slightly from the color values cited in the detailed botanical description which accurately describe the colors of the new *Lagerstroemia.*

DETAILED DESCRIPTION

Figure 1:
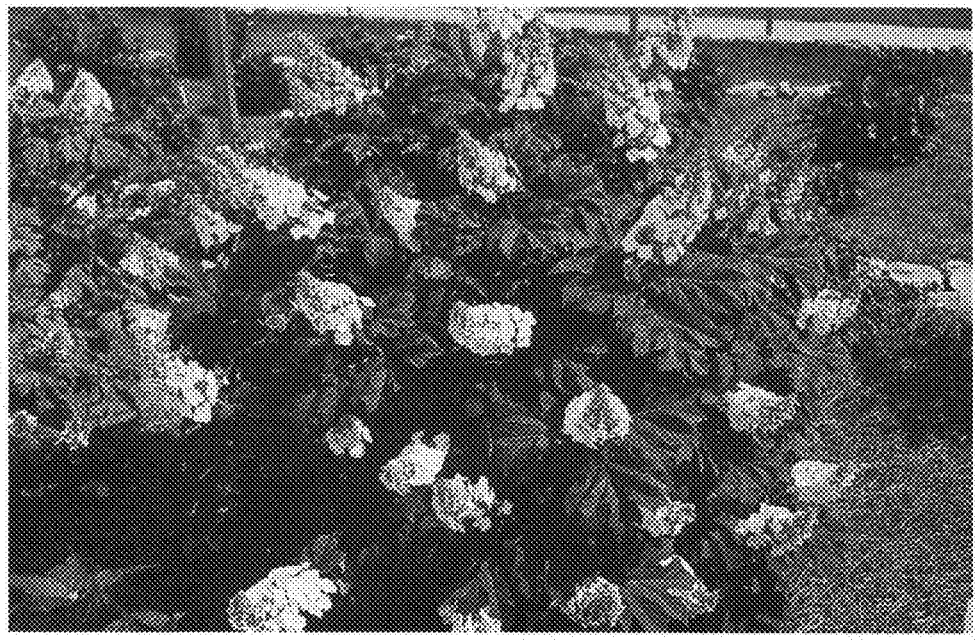
FIG. 1 illustrates the overall appearance of a plant of 'PIIHQ-I' planted in the ground.
Figure 2:
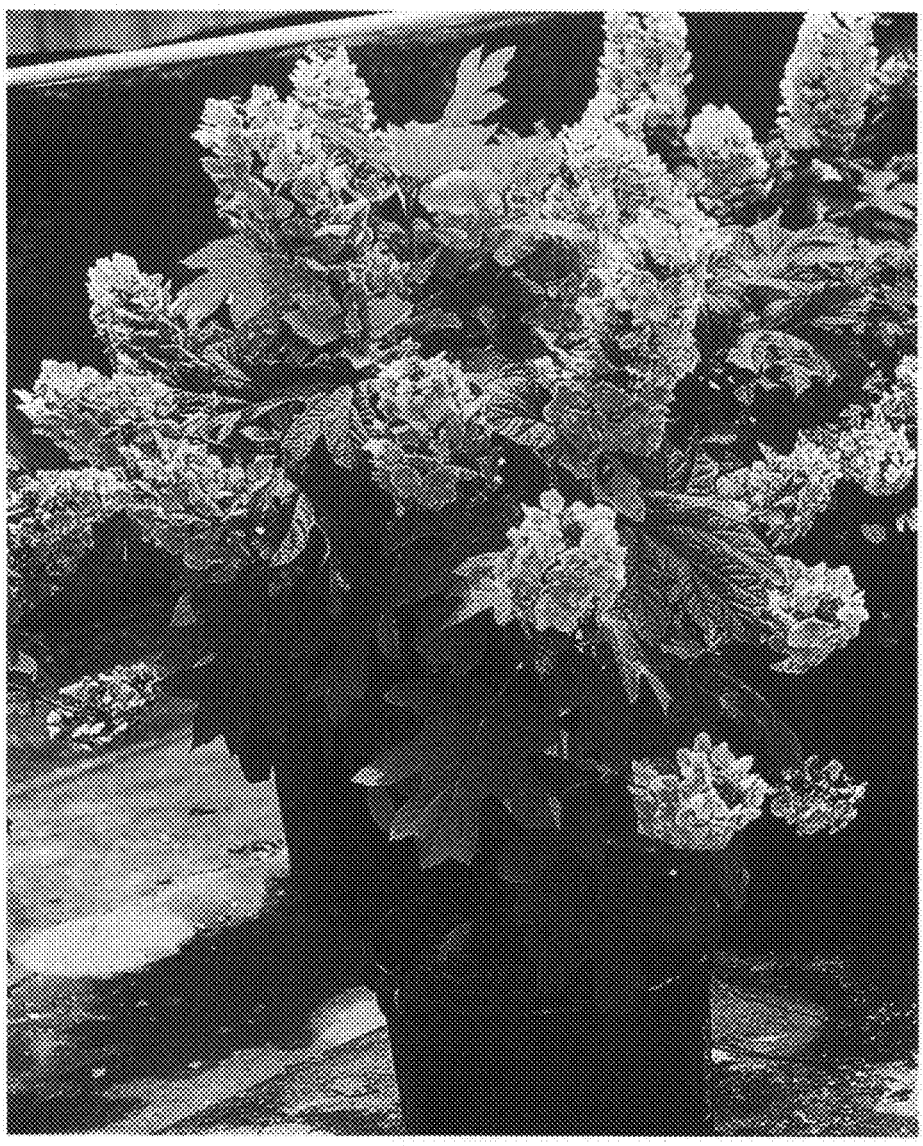
FIG. 2 illustrates the color change of the inflorescences as they age from white to light pink.
Figure 3:
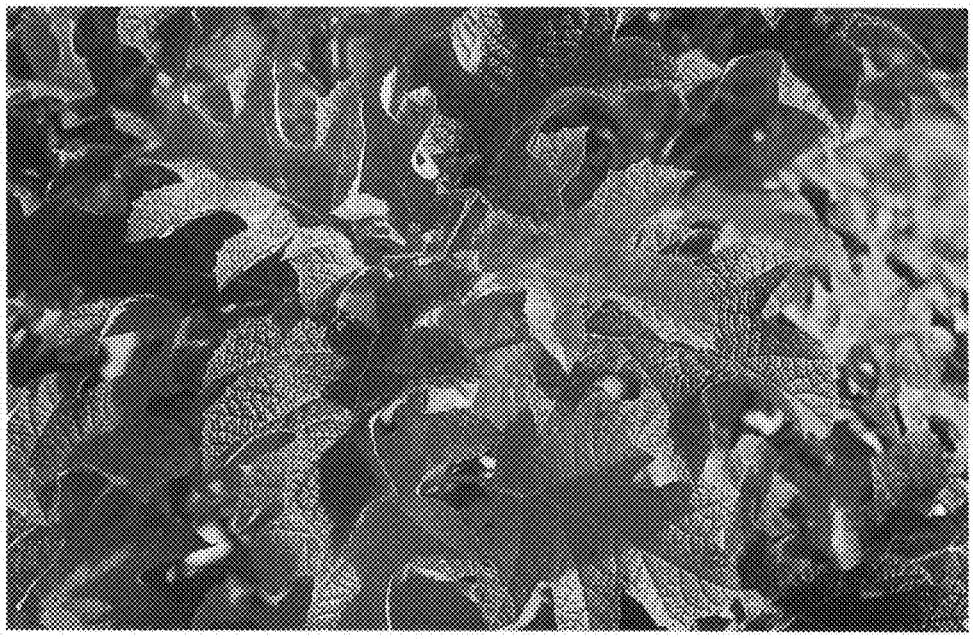
FIG. 3 illustrates the fall color of the foliage of 'PIIHQ-I'.

In the following description, color references are made to The Royal Horticultural Society Colour Chart, 2007 Edition, except where general terms of ordinary dictionary significance are used. Plants used for the description were approximately two years old and were grown in 11.8 L containers under 50% shade under outdoor conditions in Watkinsville, Ga. Colors are described using The Royal Horticultural Society Colour Chart (R.H.S.).

Botanical classification: *Hydrangea quercifolia* Bartr., cultivar 'PIIHQ-I'.

Parentage:

*Female, or seed, parent*.—An unnamed, unpatented selection of *Hydrangea quercifolia*.

*Male, or pollen, parent*.—Unkown (open-pollinated).

Propagation: Stem cuttings.

*Time to initiate roots, summer*.—About 28 days at 32° C.

Plant description: Deciduous, flowering shrub; compact, rounded to spreading growth habit. Freely branching; pruning enhances lateral branch development.

*Root description*.—Numerous, fine, fibrous and well-branched.

*Plant size*.—The original plant, now about 5-years-old in the ground, is about 132 cm high from the soil level to the top of the inflorescences and about 157 cm wide. First year stems are stout and have a diameter of about 5 mm. Shape: round. Pubescence: tomentose. Second year and older stems have a diameter of about 6 mm or more. Shape: round.

*Trunk diameter*.—3.9 cm at the soil line. Color: N199D.

*Internode length*.—About 4.3 cm.

*First year stem color* (*young*).—166D. Color (woody): 200D.

*Second year and older stem color*.—199D.

*Bark*.—Exfoliates in papery strips or sheets beginning on second or third year stems.

Vegetative buds: Opposite in arrangement, imbricate, 4 to 6 scaled, divergent, tomentose.

*Color*.—166D.

*Size*.—Lateral buds about 3 mm in length and 2.5 mm in width, terminal buds about 1.7 cm in length and 8 mm in width.

Foliage description:

*Arrangement*.—Opposite, simple.

*Length*.—About 4.5 cm.

*Width*.—About 2.8 cm.

*Shape*.—Roughly ovate in outline, usually 5 lobed, often the 5 main lobes are subdivided at the apex into 2 or 3 smaller lobes.

*Apex*.—Acuminate.

*Base*.—Truncate to subcordate.

*Margin*.—Serrate.

*Texture upper surface*.—Glabrous, sparsely pubescent.

*Texture lower surface*.—Tomentose.

*Venation pattern*.—Pinnate. Veins covered with tomentose pubescence on upper and lower surfaces.

*Venation color of emerging foliage* (*upper surface*).—191A.

*Venation color of emerging foliage* (*lower surface*).—192A.

*Venation color of fully expanded foliage* (*upper surface*).—164B.

*Venation color of fully expanded foliage* (*lower surface*).—162B.

*Color in developing foliage* (*upper surface*).—191A.

*Color in developing foliage* (*lower surface*).—192A.

*Color in fully expanded foliage* (*upper surface*).—147A.

*Color in fully expanded foliage* (*lower surface*).—191B.

*Fall color*.—N34B, 187B, or any combination of these colors.

*Petiole length*.—About 6 cm.

*Petiole diameter*.—About 4 mm.

*Petiole color* (*upper and lower surfaces*).—N199D.

*Pubescence*.—Tomentose.

Flower description: Flowers are produced from about May to June in Watkinsville, Ga. An inflorescence remains showy for about eight weeks as the flowers open white and eventually age to pink over this period of time. An inflorescence contains about 600 individual fertile flowers. An inflorescence contains about 70 individual sterile florets. Inflorescences possess a faint, sweet fragrance.

*Inflorescence type*.—Panicle.

*Inflorescence length*.—About 23 cm.

*Inflorescence width*.—About 10.6 cm.

*Peduncle*.—About 21.5 cm in length, about 4 mm in diameter, color is 166D, with tomentose pubescence.

*Pedicels*.—About 4.2 cm in length, about 1.5 mm in diameter, 144C in color, with very fine pubescence.

Fertile flowers:

*Flower buds*.—About 3 mm in length, about 2 mm in diameter, and 157A in color.

*Individual flowers*.—About 3 mm in height and 2 mm in diameter.

*Petals*.—None observed.

*Stamens*.—Usually 6 per flower, 2.5 mm in length, 0.5 mm in width, and 157D in color.

*Anthers*.—About 0.5 mm in length, about 0.5 mm in width, 149D in color.

*Pollen*.—155D in color, produced in small quantities.

*Pistil*.—Superior, about 3 mm in length, about 2 mm in width, and 157D in color.

*Stigma*.—About 0.5 mm in diameter, round in shape and 157D in color.

*Style*.—About 1.5 mm in length, tubular in shape, and 157D in color.

*Ovary*.—About 1.5 mm in diameter, round in shape, and 157D in color.

Sterile florets: Sterile florets are about 3 cm in diameter. Each floret contains 4 sepals about 1.5 cm in length and about 1.5 cm in width.

*Sepal shape*.—Broad ovate to rounded with obtuse apex, acute base, and entire margin.

*Texture*.—Smooth with no pubescence.

*Color at maturity* (*upper and lower surfaces*).—NN155B.

*Color of aged sepals* (*upper and lower surfaces*).—38B.

Fruit:

*Type/appearance*.—Dehiscent, rounded capsule.

*Length*.—About 2 mm.

*Diameter*.—About 2 mm.

*Color*.—N200A. Each capsule contains many seeds that are tiny, dust-like, and 200C in color.

Disease/pest resistance: Plants of the claimed *Hydrangea* variety grown in field and container trials have exhibited resistance to leaf spot.

We claim:

1. A new and distinct *Hydrangea quercifolia* plant named 'PIIHQ-I', substantially as illustrated and described herein.

* * * * *